United States Patent [19]
Uflacker et al.

[11] Patent Number: 5,243,997
[45] Date of Patent: Sep. 14, 1993

[54] VIBRATING DEVICE FOR A GUIDE WIRE

[75] Inventors: Renan Uflacker, San Paulo, Brazil; Thomas E. Olson, Poway, Calif.

[73] Assignee: Interventional Technologies, Inc., San Diego, Calif.

[21] Appl. No.: 944,473

[22] Filed: Sep. 14, 1992

[51] Int. Cl.⁵ .............................. A61R 5/00
[52] U.S. Cl. ..................... 128/772; 128/32; 604/22
[58] Field of Search .............. 128/657, 772, 32, 36, 128/43; 604/22

[56] References Cited

U.S. PATENT DOCUMENTS

| | | | |
|---|---|---|---|
| 3,315,663 | 4/1967 | Goldfarb | 128/32 |
| 3,589,363 | 6/1971 | Banko et al. | 128/276 |
| 3,823,717 | 7/1974 | Pohlman et al. | 128/305 |
| 3,900,023 | 8/1975 | McBride | 128/36 |
| 4,504,264 | 3/1985 | Kelman | 604/22 |
| 4,686,982 | 8/1987 | Nash | 128/305 |
| 4,696,667 | 9/1987 | Masch | 604/22 |
| 4,844,092 | 7/1989 | Rydell et al. | 128/657 |
| 4,861,332 | 8/1989 | Parisi | 604/22 |
| 4,898,575 | 2/1990 | Fischell et al. | 604/22 |
| 4,957,117 | 9/1990 | Wysham | 128/772 |
| 5,026,384 | 6/1991 | Farr et al. | 606/159 |

*Primary Examiner*—Max Hindenburg
*Attorney, Agent, or Firm*—Nydegger & Associates

[57] ABSTRACT

A hand held vibrating device for vibrating a guide wire used in angioplasty and atherectomy procedures. The vibrating device permits the guide wire to be more easily passed through a stenotic segment of a blood vessel. The vibrating device includes a case, an electric motor mounted within the case, and a clamp member coupled to the electric motor for releasably securing and vibrating the guide wire. In use, the guide wire is threaded through a blood vessel to the site of a stenosis. The guide wire can then be clamped to the vibrating device, which is selectively actuated and manipulated to vibrate and push the guide wire through the stenosis.

21 Claims, 4 Drawing Sheets

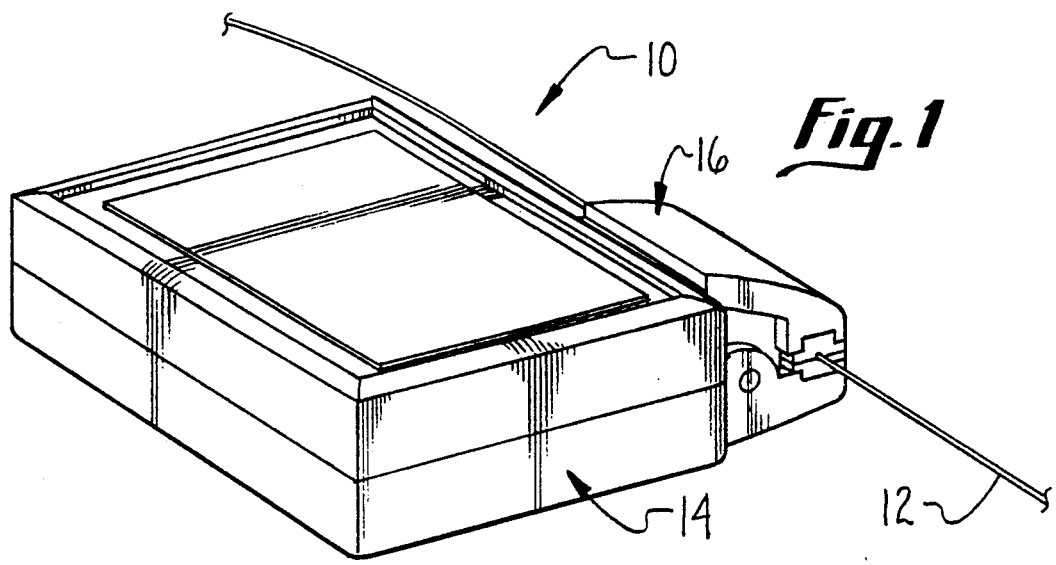
*Fig. 1*
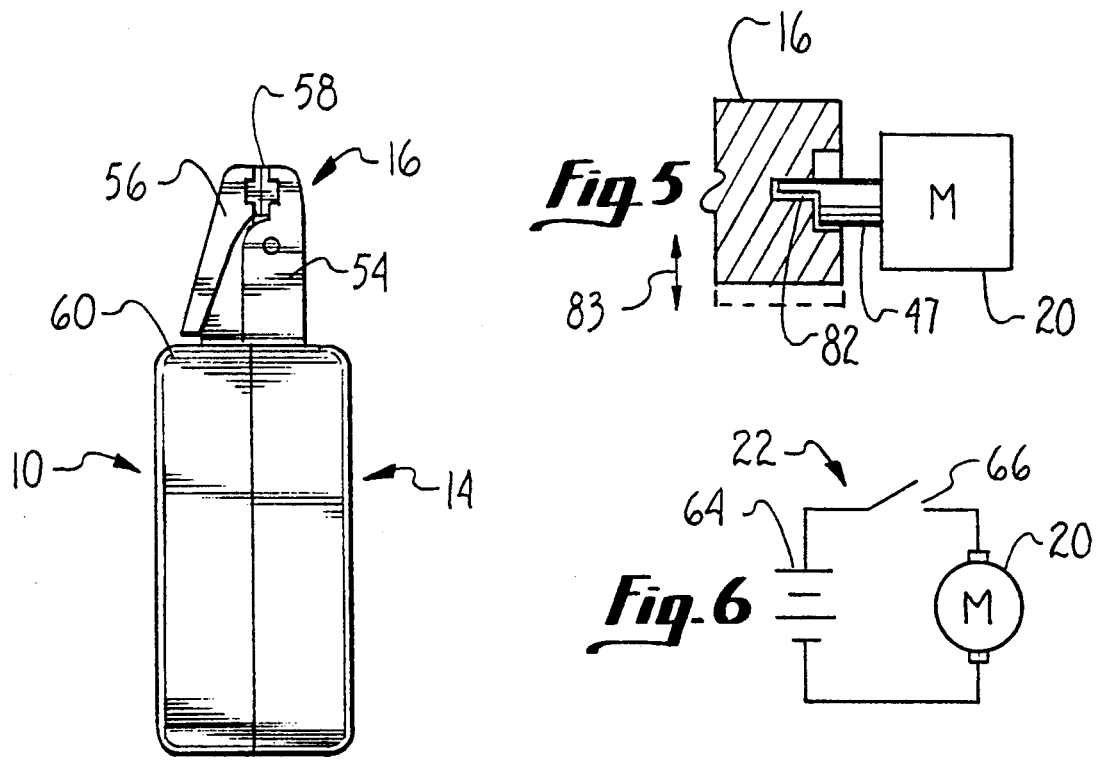
*Fig. 2*  *Fig. 5*  *Fig. 6*
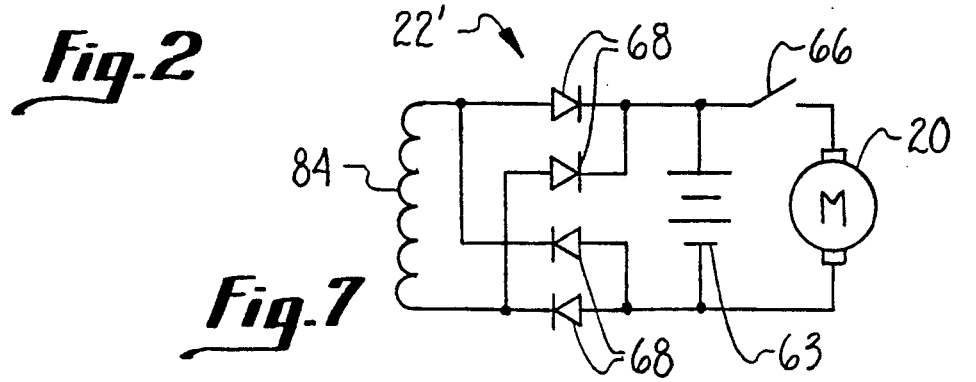
*Fig. 7*

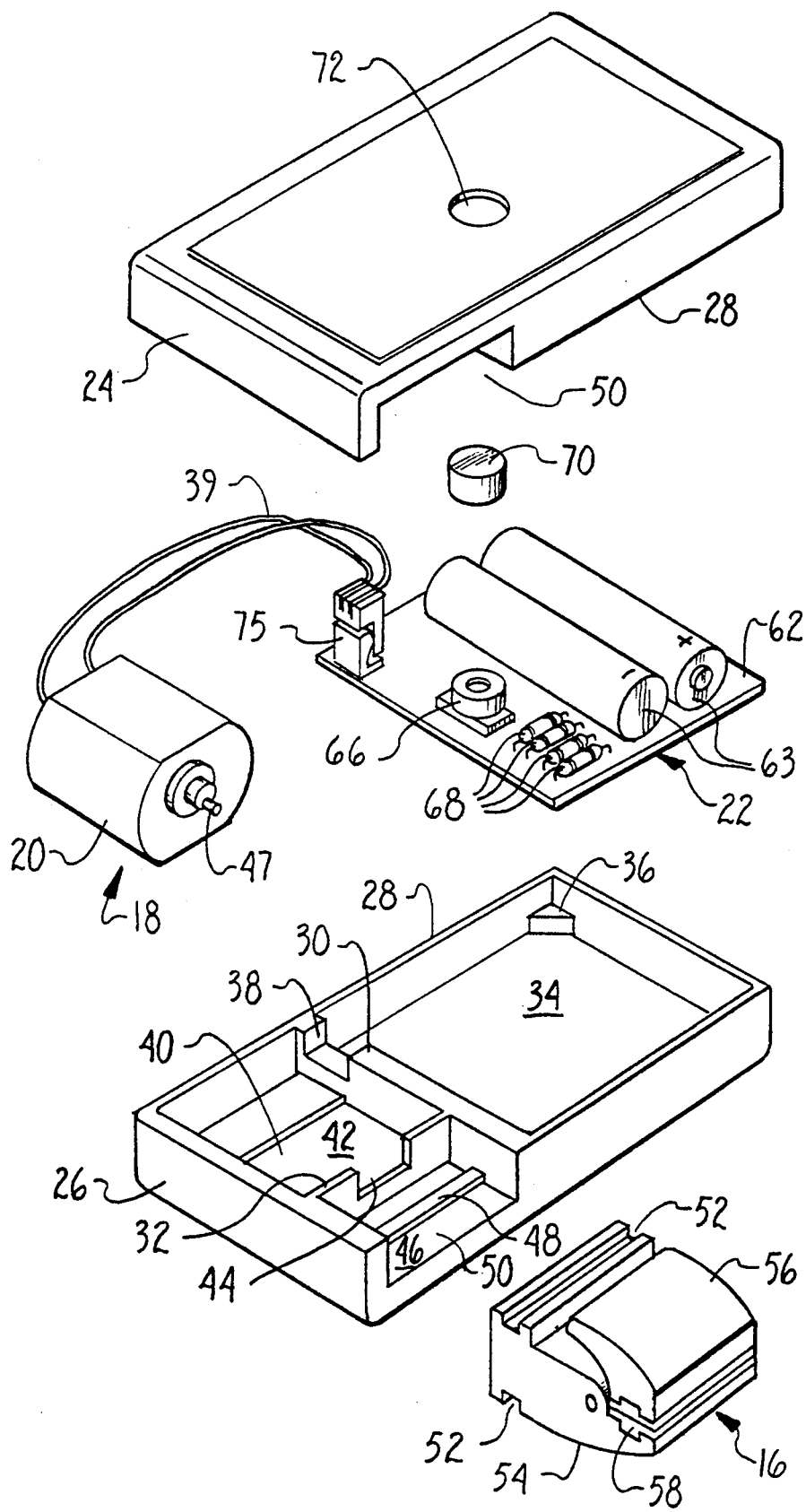

VIBRATING DEVICE FOR A GUIDE WIRE

FIELD OF THE INVENTION

The present invention relates generally to medical devices and more particularly to angioplasty and atherectomy devices for opening a stenotic segment of a blood vessel. The present invention is particularly, though not exclusively, useful with a guide wire for moving the guide wire through a stenosis so that an inflatable device or a cutter device can be positioned at the stenosis.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of arterial blockages reducing arterial blood flow. Consequently, several methods have been introduced to alleviate the effects of plaque build-up restricting the arterial lumen. One such method is a procedure termed angioplasty, which uses an inflatable device positioned in the artery to dilate the lumen at the stenosis. A typical angioplasty device is disclosed in U.S. Pat. No. 4,896,669 to Bhate et al. The angioplasty device of Bhate et al includes an inflatable balloon which is attached to the distal end of a hollow catheter. The proximal end of the catheter is attached to a fluid source, providing fluid communication between the balloon and the fluid source.

To treat an arterial stenosis, the Bhate et al balloon is introduced into the artery in a deflated state and guided through the artery over a guide wire to a position adjacent the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices, such as the Bhate et al device, do not remove the plaque from the artery. Consequently, the residual plaque either remains in place at the point of the stenosis or breaks off and migrates to other locations in the blood stream. In either case the plaque remains a continuing threat to create blockages in the circulatory system. To address the shortcomings of angioplasty, a procedure termed atherectomy has been devised which cuts and removes the plaque comprising the stenosis from the blood vessel.

An atherectomy procedure typically includes inserting a guide wire into the affected artery and advancing a hollow cutting device over the wire until the cutting device is positioned adjacent the stenosis. The cutting device is then advanced into the stenosis to cut a channel through the plaque, thereby increasing blood flow through the artery. The resulting plaque fragments are removed from the blood stream by drawing them into the hollow cutting device.

A number of atherectomy devices capable of performing this procedure are known in the art. U.S. Pat. No. 4,895,166 to Farr et al, which is assigned to the same assignee as the present invention, discloses an atherectomy device having a frustum-shaped cutter which is attached to the distal end of a hollow catheter. The cutter has two openings that define two straight, even cutting blades. The cutter is directed through the artery over a guide wire, and it is rotated as it advances into the stenosis, thereby cutting the plaque. Excised plaque enters the openings of the cutter and is subsequently removed through the hollow catheter.

A particular problem associated with angioplasty and atherectomy procedures is in moving the guide wire through the stenosis so that an inflatable balloon or cutting device can be positioned within or adjacent to the stenosis. A stenotic segment of a blood vessel presents a narrowed and often tortuous path through which the guide wire must be advanced. In some cases the stenotic segment of the blood vessel may be almost completely blocked (i.e. occluded) with atherosclerotic plaque. Accordingly the present invention recognizes the need, in the treatment of an occluded or narrowed blood vessel for a guide wire that can be easily moved through the stenotic segment of the blood vessel.

It is therefore an object of the present invention to provide a vibrating device for vibrating a guide wire such that the guide wire can be more easily moved through a stenotic segment of a blood vessel. It is another object of the present invention to provide a vibrating device that is especially adapted for use in angioplasty and atherectomy medical procedures. It is a further object of the present invention to provide a vibrating device for a guide wire that is relatively easy to use and cost effective to manufacture.

SUMMARY OF THE INVENTION

In accordance with the present invention a novel vibrating device especially adapted for use with a guide wire for angioplasty and atherectomy procedure is provided. The vibrating device simply stated includes a case, an electric motor mounted within the case, and a clamp member in contact with an output shaft of the electric motor for releasably holding and vibrating the guide wire. In use of the vibrating device, during treatment of a stenotic segment of a blood vessel, the guide wire can be introduced into the blood vessel by well known surgical techniques, and moved through the blood vessel to the stenotic segment. The vibrating device can then be used to hold and vibrate the guide wire so that it may be more easily pushed through the stenotic segment.

The vibrating device includes a case adapted to be hand held by the physician or other medical personnel during the medical procedure. The electric motor and clamp are mounted to the case. The clamp is mounted on a slide member for movement back and forth by an output shaft of the electric motor. The electric motor is manually actuated by a push button switch for intermittent operation as required. In use, the guide wire can be releasably placed within the clamp and repositioned or advanced on the clamp as the guide wire is vibrated and pushed through the stenosis.

The novel features of this invention, as well as the invention itself, both as to its structure and its operation, will be best understood from the accompanying drawings, taken in conjunction with the accompanying description, in which similar reference characters refer to similar parts.

BRIEF DESCRIPTION OF THE DRAWINGS

FIG. 1 is a perspective view of a vibrating device for a guide wire constructed in accordance with the invention;

FIG. 2 is a side elevation view of the vibrating device shown in FIG. 1;

FIG. 3 is an exploded perspective view of the vibrating device shown in FIG. 1 showing the assembly of the device;

FIG. 5 is a schematic cross sectional view of a vibrating motor and a portion of a clamp member of the vibrating device of the invention showing mechanical coupling of the clamp and motor;

FIG. 6 is an electrical schematic of a control circuit for the vibrating device; and FIG. 7 is an electrical schematic of an alternate embodiment control circuit for a vibrating device having rechargeable batteries.

DESCRIPTION OF PREFERRED EMBODIMENTS

Figure 4:
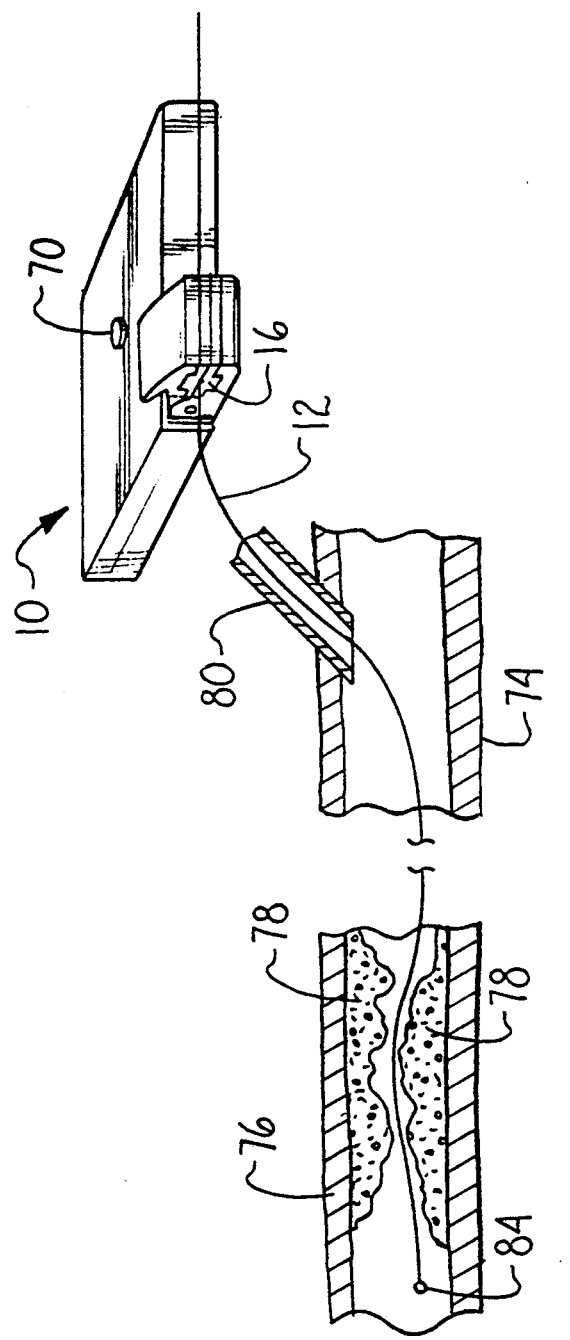
FIG. 4 is an enlarged schematic cross sectional view of a stenotic segment of a blood vessel showing a vibrating guide wire being pushed through a stenotic segment of a blood vessel.

Referring to FIGURES and 2 a vibrating device constructed in accordance with the invention is shown and generally designated as 10. The vibrating device 10 is adapted to hold and vibrate an elongated guide wire 12 which can be used in a medical procedure such as an angioplasty or atherectomy procedure as previously described, in which the guide wire 12 is pushed through a stenotic segment of a blood vessel. Use of the vibrating device 10, is not restricted to a guide wire 10, however, as it may be utilized to move other medical devices such as a hollow wire or an elongated catheter through a blood vessel.

The vibrating device 10, broadly stated, includes; a case 14; holding means in the form of a clamp member 16 slidably mounted to the case for releasably holding the guide wire 12; and vibrating means 18 in the form of a vibrating motor 20 and control circuit 22 for vibrating the clamp 16 and the guide wire 12 positioned within the clamp 16.

The case 14 is adapted to be hand held by the physician while the guide wire 12 is pushed through the blood vessel. As such, the case 14 is sized and shaped to fit easily in a person's hand while the guide wire 12 and clamp 16 are manipulated. The case 14 has a generally rectangular outer peripheral configuration and as shown in FIG. 3 is formed in two mating halves. The case 14 may be formed of a sturdy, cleanable, material such as molded plastic.

With reference to FIG. 3 the case 14 includes a top portion 24 and a mating bottom portion 26. The top portion 24 and bottom portion 26 of the case 14 are formed in a mirror image of one another. This construction includes a peripheral edge 28 that extends generally perpendicular from a top or bottom surface of the case 14 and a pair of internal ribs 30, 32. With the top portion 24 of the case assembled to the bottom portion 26 the placement of the internal ribs 30, 32 forms three separate compartments within the interior of the closed case 14.

A first generally rectangular shaped compartment 34 formed within the closed case 14 houses the control circuit 22 (i.e. electrical components) for the vibrating motor 20. The control circuit compartment 34 is generally rectangular in shape and corresponds to the outer peripheral shape of a printed circuit board 22 for the control circuit 22. Triangular shaped standoffs 36 are formed in each corner of the control circuit compartment 34 for mounting the printed circuit board 62 within the control circuit compartment 34. A recess 38 is formed in the internal ribs 30 (top and bottom) which form the control circuit compartment 34. With the top portion 24 and bottom portion 26 of the case 14 assembled the mating recesses 38 in the internal ribs 30 form an opening for electrical wiring 39 from the circuit board 62 to the vibrating motor 20.

A second generally rectangular shaped compartment 40 formed within the closed case 14 houses the vibrating motor 20. The vibrating motor compartment 40 is generally rectangular in shape and corresponds to the outer peripheral shape of the vibrating motor 20. The vibrating motor 20 rests on an indented surface 42 within the compartment 40. A recess 44 is formed in the internal ribs 32 (top and bottom) which form the vibrating motor compartment 40. With the top portion 24 and bottom portion 26 of the case 14 assembled the mating recesses 44 in the internal ribs 32 form an opening for an output shaft 47 of the vibrating motor 20 which contacts and imparts vibratory motion to the clamp 16 and to a guide wire 12 secured to the clamp 16.

A third generally rectangular shaped compartment 46 formed within the closed case 14 houses the clamp 16 for the guide wire 12. The clamp compartment 46 is generally rectangular in shape and corresponds in shape to the outer peripheral shape of the clamp 16. The clamp 16 is slidably mounted within the clamp compartment 46 for rapid lateral back and forth or vibratory motion. A mounting track 48 is located within the clamp compartment 46 for mounting the clamp 16 which is slidably mounted on this mounting track 48. The clamp compartment 46 is dimensioned with a width that is larger than the width of the clamp 16 such that the clamp 16 has a range of motion (i.e. back and forth laterally) within the clamp compartment 46. In addition, as before recesses are formed in the peripheral edge 28 of the top portion 24 and bottom portion 26 of the case 14 such that in the assembled or closed case 14 an opening 50 is formed for the clamp 16.

The clamp 16 is mounted within the clamp compartment 46 of the case 14 and is coupled to an eccentric output shaft 47 of the vibrating motor 20. The clamp 16 includes mounting recesses 52 that correspond to the mounting tracks 48 of the clamp compartment 46. The clamp 16 is thus free to move laterally or slide back and forth along the mounting track 48. In operation of the vibrating device 10, the clamp 16 is driven back and forth along the mounting track 48 by the vibrating motor 20. This provides the vibratory motion which is then imparted to a guide wire 12 releasably held in the clamp 16. This vibratory motion is confined to a single plane (i.e. lateral or horizontal) as the clamp is free to move in only a single plane and cannot move in a vertical plane. The dimensioning of the clamp compartment 46 prevents vertical movement of the clamp and at the same time limits the horizontal motion or stroke of the vibratory motion of the clamp 16.

FIG. 5 illustrates the mechanical coupling of the clamp 16 to the vibrating motor 20. The clamp 16 is formed with a stepped or counterbored slot 82 that is sized to mate with the electric output shaft 47 of the vibrating motor 20. The electric output shaft 47 has a stepped construction, substantially as shown in FIG. 3, that corresponds to the stepped or counterbored slot 82 of the clamp. As is apparent, rotational motion of the eccentric output shaft 47 of the vibrating motor 20 translates into back and forth or vibratory movement of the clamp 16, as indicated by double headed arrow 83 in FIG. 5.

Figure 8:
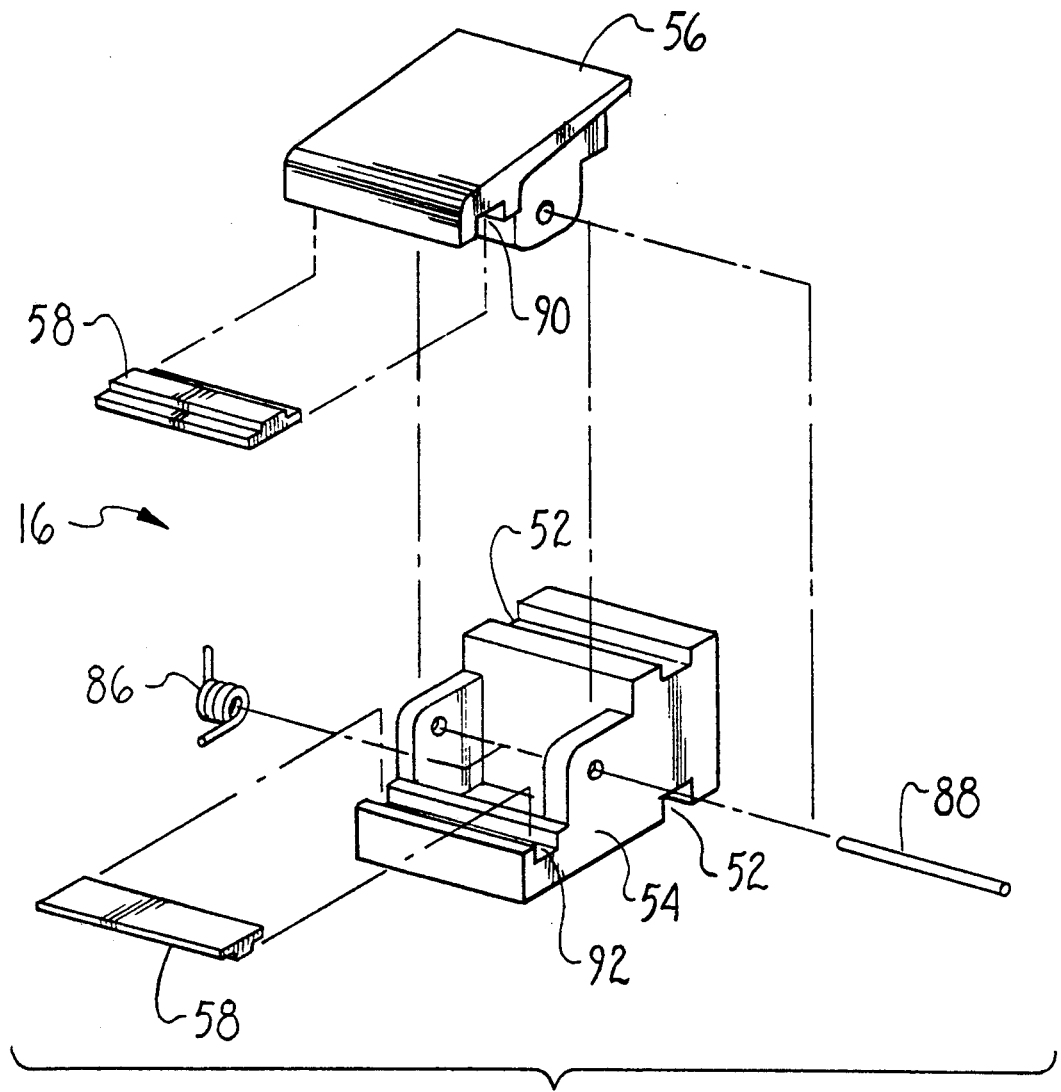
FIG. 8 is an exploded perspective view of the clamp member of the vibrating device.

Referring now to FIGS. 3 and 8, for releasably holding the guide wire 12, the clamp 16 includes a stationary portion 54 and a moveable clip portion 56 hingedly mounted to the stationary portion 54 on a hinge pin 88 (FIG. 8). A spring member 86 (FIG. 8) biases the clip portion 56 in a closed position against the stationary portion 54 of the clamp 16. Resilient contact members 58 of a material such as urethane or rubber are mounted in a slot 90 and 92 (FIG. 8) formed on the clip portion 56 and on the stationary portion 54 of the clamp 16 respectively.

With this arrangement the guide wire 12 can be pinched or held between the clip portion 56 and stationary portion of the clamp 16 in contact with the resilient contact members 58. As shown in FIG. 2, the clamp 16 extends from a sidewall 60 of the case 14 and is positioned such that the movable clip portion 56 of the clamp 16 can be manipulated by the physician while the vibrating device 10 is held in the physician's hand. A vibrating guide wire 12 can thus be continuously advanced through the blood vessel using the clamp 16 to alternately hold and release the guide wire 12.

A suitable control circuit 22 for the vibrating device 10 is shown in FIG. 6. In its simplest form the control circuit 22 includes a power source such as a battery 64, and a normally open on-off switch 66 for operating the vibrating motor 20. As an example, the battery 64 may be a AA 1.5 volt disposable alkaline battery. Two such batteries 64 may be coupled together to provide a 3 volt power source. Alternately as shown in FIG. 7, rechargeable batteries 63 (i.e. NiCad) may be used with a control circuit 22'. This recharging control circuit 22' includes diodes 68 and an inductive element 84.

As shown in FIG. 3, the electrical components of the control circuit 22 or 22' for the vibrating device 10 are mounted on the printed circuit board 62. An externally mounted push button 70 operates the on-off switch 66 for actuating the vibrating motor 20. An opening 72 is formed in the top portion 24 of the case 14 for accessing the push-button 70. The printed circuit board 62 also includes a connector 75 which connects wiring 39 from the vibrating motor 20 to components located on the printed circuit board 62.

As previously explained the vibrating motor 20, is adapted to contact the clamp 16 and impart a vibratory motion to the clamp 16 and to a guide wire 12 held within the clamp 16. A suitable vibratory motor 20 has a small fractional horsepower output and turns at relatively high rpm's (i.e. 8000 rpms). Motors that operate at much lower revolutions, however, as low as 100 rpm, are also suitable for this application. The frequency with which the guide wire 12 will vibrate will be directly proportional to the revolutions of the vibrating motor 20. In general off the shelf motors having a modified output shaft are suitable for this application. Unlike the clamp member 16 which is free to vibrate in only a single plane (i.e. laterally) the guide wire within the blood vessel will vibrate in three dimensions. The main thrust of the vibration however will be back and forth to facilitate advancement through a stenosis.

OPERATION

Referring now to FIG. 4 the vibrating device 10 of the invention is shown in use. A blood vessel such as an artery 74 includes a stenotic segment 76 wherein a build up of atherosclerotic plaque 78 is located. In order to perform an angioplasty or atherectomy procedure a guide wire 12 must be pushed through the stenotic segment 76 to locate an inflatable balloon or outter device within the stenotic segment 76. Initially, the guide wire 12 is placed into the artery 74 utilizing an introductory catheter 80 that is percutaneously inserted into the artery 74. The guide wire 12 can then be directed through the artery 74 to the stenotic segment 76 of the artery 74 utilizing well known surgical techniques such as radiological techniques. The guide wire 12 may in fact be formed with a radiopaque tip 84 at its distal end to facilitate such a procedure.

The proximal end of the guide wire 12 can then be fastened to the clamp 16 of the vibrating device 10 so that the guide wire 12 can be vibrated and pushed through the stenotic segment 76 of the artery 74. The build up of plaque 78 in the artery 74 would normally make it difficult to pass the guide wire 12 through the stenotic segment 76. By selectively actuating the vibrating motor 20 to vibrate the guide wire 12, however, the physician is more easily able to direct the guide wire 12 through the plaque 78. The vibrating guide wire 12 in effect finds an open channel through the plaque 78 or alternately cuts its own path through the plaque.

The clamp 16 of the vibrating device 10 can be used to hold the guide wire 12 while it is advanced through the stenotic segment and to alternately grip and release the guide wire 12 while the proximal end of the guide wire 12 is relocated with respect to the vibrating device 10. During this procedure the vibrating device 10 is held in the physician's hand. The physician operates the push button 70 which controls the vibrating motor 20 and manipulates the guide wire 12 and clamp 16 as required.

Thus the vibrating device of the invention provides a simple yet unobvious device for vibrating a wire, particularly suited to angioplasty and atherectomy procedures. While the particular vibrating device for a guide wire as herein shown and disclosed in detail is capable of obtaining the objects and providing the advantages hereinbefore stated, it is understood that this particular device is merely illustrative of presently preferred embodiments of the invention. It is further understood that the present invention is not intended to be so limited and that other embodiments are further possible within the scope of the present invention.

I claim:

1. In a procedure wherein a guide wire or the like is placed through a blood vessel, a vibrating device for facilitating passage of the guide wire through the blood vessel, said vibrating device comprising:
   holding means for releasably holding the guide wire; and
   vibrating means coupled to the holding means for vibrating the guide wire such that the guide wire may be held and advanced through the blood vessel.

2. The vibrating device as recited in claim 1 and wherein the holding means includes:
   clamp means for releasably securing the guide wire.

3. The vibrating device as recited in claim 2 and wherein:

the clamp means includes a resilient member for contacting the guide wire.

4. The vibrating device as recited in claim 3 and the vibrating means includes an electric motor.

5. The vibrating device as recited in claim 4 and wherein:

electric motor and clamp means are mounted to a case adapted to be hand held.

6. The vibrating device as recited in claim 5 and wherein:

the clamp means is movably mounted to the case in contact with an output shaft of the electric motor.

7. A vibrating device for vibrating a guide wire useful in an angioplasty or atherectomy procedure comprising:

a case sized and shaped to be hand held;
a vibrating motor mounted within the case and having an output member;
a clamp member slidably attached to the hand held case in contact with the output member of the vibrating motor for releasably holding the guide wire and for vibrating the guide wire; and
control means for selectively actuating the vibrating motor.

8. The vibrating device as recited in claim 7 and wherein:

the vibrating motor is an electric motor having an output shaft that moves the clamp member back and forth in a single plane.

9. The vibrating device as recited in claim 8 and wherein:

the control means includes a control circuit formed on a circuit board mounted within the case.

10. The vibrating device as recited in claim 9 and wherein:

the vibrating motor is battery operated.

11. The vibrating device as recited in claim 10 and wherein:

the clamp member includes a base portion and a clip portion each having a resilient member for contacting the guide wire.

12. The vibrating device as recited in claim 11 and wherein:

the control means includes an on-off switch for actuating the vibrating motor.

13. In an angioplasty or atherectomy procedure wherein a guide wire is introduced into a blood vessel and guided through the blood vessel to a stenosis located in the blood vessel, a vibrating device for vibrating the guide wire such that it may be more easily guided through the stenosis, said vibrating device comprising:

a case sized and shaped to be hand held;
an electric vibrating motor mounted within the case and including an output shaft;
a control circuit for operating the vibrating motor mounted within the case and coupled to a power source and to a switch for operating the motor; and
a clamp member for releasably holding the guide wire with the clamp member slidably mounted to the case in contact with the output shaft of the vibrating motor for movement by the vibrating motor.

14. The vibrating device as recited in claim 13 and wherein:

the clamp member includes a counterbored slot that mates with a stepped output shaft of the vibrating motor.

15. The vibrating device as recited in claim 14 and wherein:

the clamp member is slidably mounted on the case for movement in a lateral plane.

16. The vibrating device as recited in claim 15 and wherein:

the clamp member includes a mounting slot that mates with a mounting track formed on the case.

17. The vibrating device as recited in claim 16 and the clamp member includes a resilient member for contacting the guide wire.

18. The vibrating device as recited in claim 17 and the switch for operating the motor includes an exposed push button for manual actuation.

19. The vibrating device as recited in claim 18 and wherein:

the power source for the vibrating motor is a battery mounted to a printed circuit board in the case.

20. The vibrating device as recited in claim 19 and wherein:

the control circuit is configured for recharging the battery with an external power source.

21. The vibrating device as recited in claim 19 and wherein:

the case is formed with a top portion and a bottom portion including internal ribs to form separate compartments for the clamp member, the printed circuit board, and the motor.

* * * * *